United States Patent [19]

Callaway

[11] Patent Number: 5,649,929
[45] Date of Patent: Jul. 22, 1997

[54] KNEE JOINT FLEXION-GAP DISTRACTION DEVICE

[76] Inventor: George Hadley Callaway, 2719 St. Mary's St., Raleigh, N.C. 27609

[21] Appl. No.: 500,732

[22] Filed: Jul. 10, 1995

[51] Int. Cl.$^6$ .................................................. A61B 17/56
[52] U.S. Cl. .......................... 606/88; 606/87; 606/90
[58] Field of Search ............................ 606/80, 86, 87, 606/88, 90; 600/208, 210, 219, 222, 225, 226

[56] References Cited

U.S. PATENT DOCUMENTS

| | | |
|---|---|---|
| D. 262,055 | 11/1981 | Luikart, II . |
| 3,750,652 | 8/1973 | Sherwin . |
| 3,840,014 | 10/1974 | Ling et al. . |
| 3,916,907 | 11/1975 | Peterson ................................ 606/219 |
| 4,066,082 | 1/1978 | Arcan et al. . |
| 4,220,146 | 9/1980 | Cloutier . |
| 4,474,177 | 10/1984 | Whiteside . |
| 4,501,266 | 2/1985 | McDaniel . |
| 4,524,766 | 6/1985 | Petersen ................................ 606/88 |
| 4,566,448 | 1/1986 | Rohr, Jr. . |
| 4,566,488 | 1/1986 | Rohr, Jr. ................................ 606/88 |
| 4,567,885 | 2/1986 | Androphy . |
| 4,567,886 | 2/1986 | Peterson . |
| 4,646,729 | 3/1987 | Kenna et al. ........................... 606/80 |
| 4,722,330 | 2/1988 | Russell et al. . |
| 4,787,383 | 11/1988 | Kenna . |
| 4,825,857 | 5/1989 | Kenna . |
| 4,898,161 | 2/1990 | Grundei . |
| 4,935,023 | 6/1990 | Whiteside et al. . |
| 4,938,762 | 7/1990 | Wehrli . |
| 5,002,547 | 3/1991 | Poggie et al. ........................... 606/90 |
| 5,053,037 | 10/1991 | Lackey . |
| 5,116,338 | 5/1992 | Poggie et al. ........................... 606/90 |
| 5,213,112 | 5/1993 | Niwa et al. . |
| 5,234,433 | 8/1993 | Bert et al. . |
| 5,263,498 | 11/1993 | Caspari et al. . |
| 5,431,653 | 7/1995 | Callaway ................................ 606/90 |
| 5,464,406 | 11/1995 | Ritter et al. ............................ 606/87 |
| 5,540,696 | 7/1996 | Booth, Jr. et al. ...................... 606/90 |

*Primary Examiner*—Michael Buiz
*Assistant Examiner*—Julian W. Woo
*Attorney, Agent, or Firm*—Darby & Darby

[57] ABSTRACT

A knee distraction device is provided for use in knee arthroplasty. A mechanism applies to an adjustable distraction force between the tibial surface and a point on the distal femur of the flexed knee. The spatial relationship of tibia and femur is allowed to change by rotation of the femur around an axis between the center of the hip and the intercondylar area of the distal femur. As the distraction force is applied, relative tensions in the medial and lateral ligamentous structures of the knee are equalized by changes in the spatial relationship of the femur and tibia. During maintenance of distraction, the posterior femoral bone cut may be positioned at a predetermined distance from the cut tibial surface. The use of this mechanism facilitates accurate sizing of the flexion gap and optimal positioning of knee arthroplasty.

6 Claims, 7 Drawing Sheets

KNEE JOINT FLEXION-GAP DISTRACTION DEVICE

The present invention relates to a knee joint distraction device for facilitating knee arthroplasty, especially total knee arthroplasty.

BACKGROUND OF THE INVENTION

Primary objectives of knee arthroplasty include restoration of limb alignment, ligament balance, and joint surface contours. Restoration of limb alignment in extension reduces asymmetric loading of the bicondylar design, probably reducing the risk of component loosening. Restoration of ligament balance and joint surface contours prevents instability and restores normal joint kinematics.

Surgical instrumentation serves to simplify and standardize the implantation procedure. Several operative techniques have been advocated, differing in instrumentation and in the sequence of bone cuts. The present invention may be usefully employed in any of the several techniques.

A total knee joint prosthesis typically includes a tibial platform and a femoral component having condyler portions adapted to rest in complementary surfaces of the tibial component. Restoration of ligament balance requires careful positioning of these tibial and femoral components and selective lengthening of contracted ligamentous or soft-tissue structures. Ideally, the ligaments should be balanced at every position of knee flexion. To simplify the surgical technique, the ligament balance is checked mainly at full knee extension and at 90° knee flexion.

Extension Balancing

In full extension, both limb alignment and ligament balance must be restored. The distal femoral bone cut is made perpendicular to the axis between the centers of the hip and knee joints. The proximal tibial cut is made perpendicular to the longitudinal axis of the tibial shaft. Contracted ligaments and soft tissues are then lengthened by partial release as needed to equalize their length and tension in extension. After these bone and soft tissue cuts are made, the gap between distal femoral surface and proximal tibial surface (the extension gap) should accommodate the combined thickness of the tibial and femoral components, with the medial and lateral knee ligaments equally tensioned to provide stability.

Historically, ligament balance in extension has been addressed by the use of either spacer blocks or a joint distraction instrument. Spacer blocks are oval, metallic shims of the approximate shape and size of the proximal tibial platform. After proximal tibial and distal femoral cuts are made, spacer blocks of increasing thickness are placed in the extension gap. Gentle medial (valgus) and lateral (varus) stresses are applied to the knee by the surgeon, and the relative lengths and tensions of medial and lateral ligaments are assessed. Incremental releases are performed as needed to balance the ligaments.

In the alternative technique, a joint distraction instrument is placed between the distal femoral condyles and the previously cut proximal tibial surface during full knee extension. When the force between each condyle and the tibia is equal, the ligaments are equally tensioned. Partial ligament releases are then performed while maintaining equal ligament tension. When the proper ligament alignment is restored, the distal femoral cut is made parallel to the proximal tibial cut.

Flexion Balancing

In 90° knee flexion, ligament balance can be restored by changing the alignment of the posterior femoral bone cut. The tibial cut and soft tissue releases also affect the flexion gap, but these factors are predetermined by the requirements of limb alignment and ligament balance in extension. Historically, the posterior femoral bone cut has been positioned by posterior condyle referencing or by the use of a joint distraction instrument.

Posterior condyle referencing involves empirically positioning the posterior femoral cut to remove slightly more medial than lateral femoral condyle. This external rotation of the cut corrects the most common clinical situation, where the flexion gap is tight medially. However, the posterior condyle referencing technique becomes difficult when the condyles are eroded or when a severe pre-operative deformity exists. Technical errors are possible which may cause malfunction of the implanted knee prosthesis.

A joint distraction instrument places a distracting force between each of the posterior femoral condyles and the previously cut tibial surface during 90° knee flexion. If the force between each condyle and the tibia is equal, the ligaments will be nearly equally tensioned. If the extension gap has already been balanced, the position of the posterior femoral cut can then be measured from the proximal tibial surface to create a flexion gap of the appropriate size and shape. The joint distraction technique for flexion gap balancing is appealing in theory, but joint distraction instruments in the prior art are difficult to use. Because of shortcomings of such instrumentation, many surgeons use the easier but less reliable posterior condyle referencing technique for positioning the posterior femoral bone cut.

U.S. Pat. No. 5,116,338 to Poggie (1992) describes a flexion gap distractor which fits into the space between posterior condyles and tibial plateau. The device suffers from a number of disadvantages. It must be forced into a tight space between the posterior condyles and the tibial plateau. The portions of the device which articulate with the posterior femoral condyles fit poorly with very large and very small to knees. Medial and lateral tension adjustments are separate and tactile feed-back of tension is poor, making it difficult to achieve equal tension in the medial and lateral soft-tissues. The size of the device obstructs visualization of the knee joint and obstructs access to the anterior tibial plateau, preventing the use of spacer blocks to position the posterior femoral cut.

U.S. Pat. No. 4,938,762 to Wehrli (1990) describes a flexion gap distractor which attaches to the tibial shaft with a bone screw and engages the femoral intercondylar notch with a bent metallic arm. This device also suffers from a number of disadvantages. The need for a screw in an uninvolved and remote portion of the tibia creates undesirable morbidity. The distraction device is free to rotate around the tibial bone screw and therefore does not control medial to lateral motion of the femur relative to the tibia. Such medial or lateral motion can alter the soft-tissue balance in a deceptive manner. Finally, no means is provided for measuring the space between proximal tibial cut and the proposed posterior femoral cut.

SUMMARY OF THE INVENTION

The present invention concerns an improvement in knee arthroplasty instrumentation, especially applicable to the flexion gap balancing step of implantation. In a preferred embodiment, the invention includes a knee joint distractor which includes tibial and femoral levers pivotally connected so that by squeezing one end, the opposite ends are separated. The femoral lever includes an intramedullary rod adapted to be received in the intramedullary canal of the femur. The tibial lever terminates in a platform which is adapted to rest on the flat proximal surface of the tibia.

The invention allows the application of a distraction force between the tibia and a single point near the intercondylar notch of the distal femur of the flexed knee. The femoral contact point is maintained in a fixed medial to lateral position relative to the tibia. The femur is allowed to rotate on an axis between the hip joint and the area of the intercondylar notch. When the distraction force is applied, the femur rotates until the medial and lateral ligaments of the knee are equally tensioned.

During maintenance of distraction, a cutting guide and spacer block may be used to place the posterior femoral cut at a predetermined distance from the cut tibial surface. Alternatively, the tibial platform may support the cutting guide to position the posterior femoral cut, with spacer shims used if necessary to adjust the position of the cut. By this technique, the size and shape of the flexion gap may be accurately matched to the thickness of the arthroplasty implant.

OBJECTS AND ADVANTAGES

Several objects and advantages of the present invention are:

(a) to provide a means for tensioning equally the medial and lateral ligaments and soft tissues of the flexed knee while controlling the medial to lateral relationship of the femur and tibia;

(b) to provide a means for positioning the posterior femoral cut during total knee arthroplasty in a manner which creates a flexion gap of predetermined size and shape;

(c) to provide an instrument for flexion gap distraction which is simplified in design and use relative to prior art;

(d) to provide an instrument for flexion gap distraction which may be operated with one hand, which may be advantageous in a surgical procedure;

(e) to provide an instrument for flexion gap distraction which is less bulky than similar prior art devices and which therefore allows visualization of the knee during distraction;

(f) to provide an instrument for flexion gap distraction which allows access to the anterior portion of the cut tibial surface during distraction, thereby making it possible to use a spacer block, shim or other measuring device to position the posterior femoral cut at a predetermined distance from the cut tibial surface; and (g) to provide an instrument for flexion gap distraction which provides tactile feedback regarding soft tissue tension through a hand-held squeeze grip.

Still further objects and advantages will become evident from a consideration of the ensuing description and drawings.

DESCRIPTION OF THE INVENTION

Figure 1:
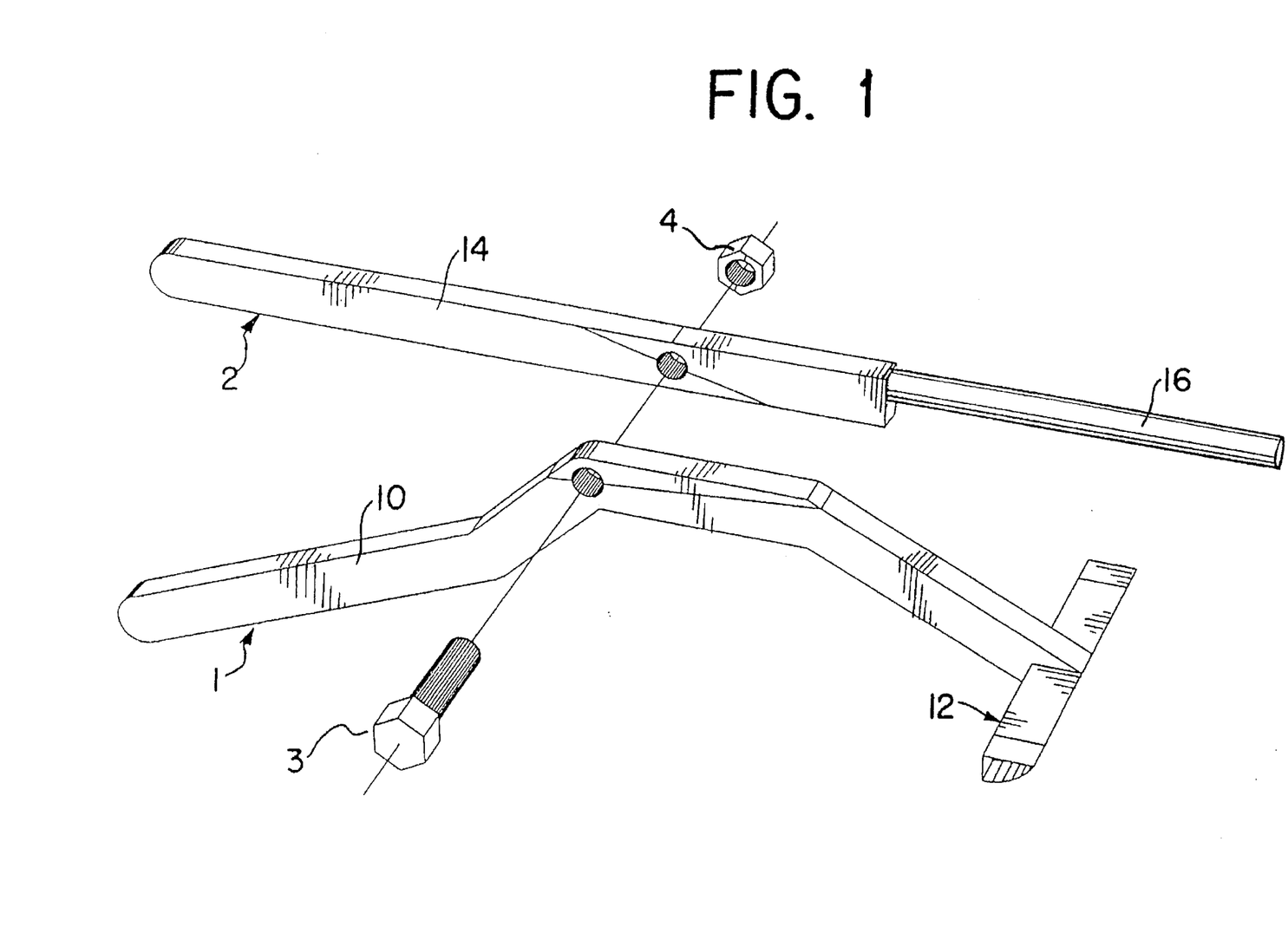
FIG. 1 shows a perspective view of the components of a preferred embodiment of a knee flexion gap distraction device according to the present invention.
Figure 2:
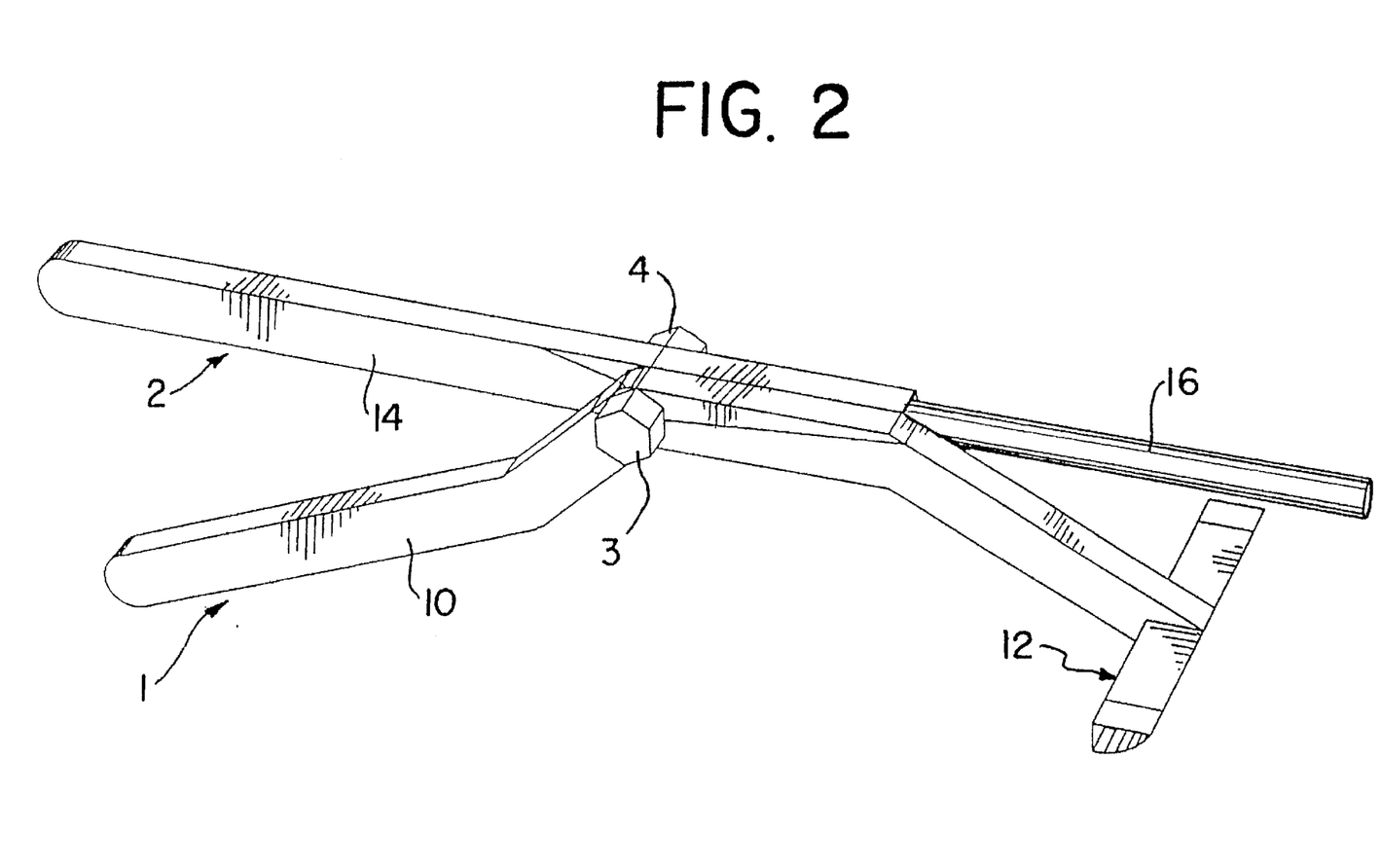
FIG. 2 shows a perspective view of the assembled components of FIG. 1.

A typical embodiment of the knee flexion gap distraction device is illustrated in FIGS. 1 and 2. The femur 13 is shown at 13 and the tibia at 15. The present invention includes a tibial device 1 with a contoured handle 10 and a broad, T-shaped platform 12 on the opposite end. A femoral device 2 has a contoured handle 14 and a cylindrical opposite end 16. Tibial device 1 and femoral device 2 are pivotally joined by a bolt 3 and nut 4 to form a hinge.

Figure 3:
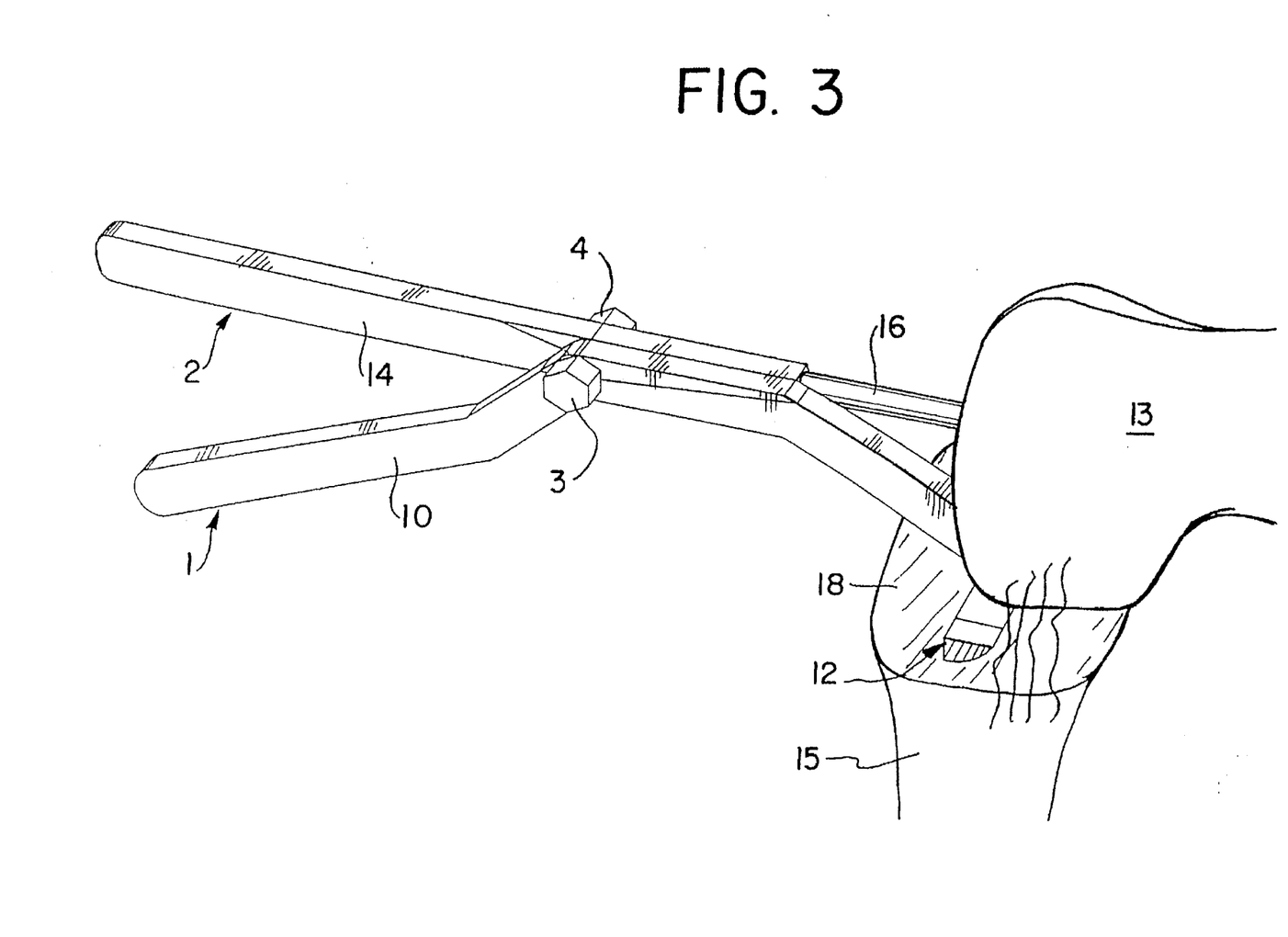
FIG. 3 shows a typical embodiment of the present invention on a flexed knee before application of a distraction force.
Figure 4:
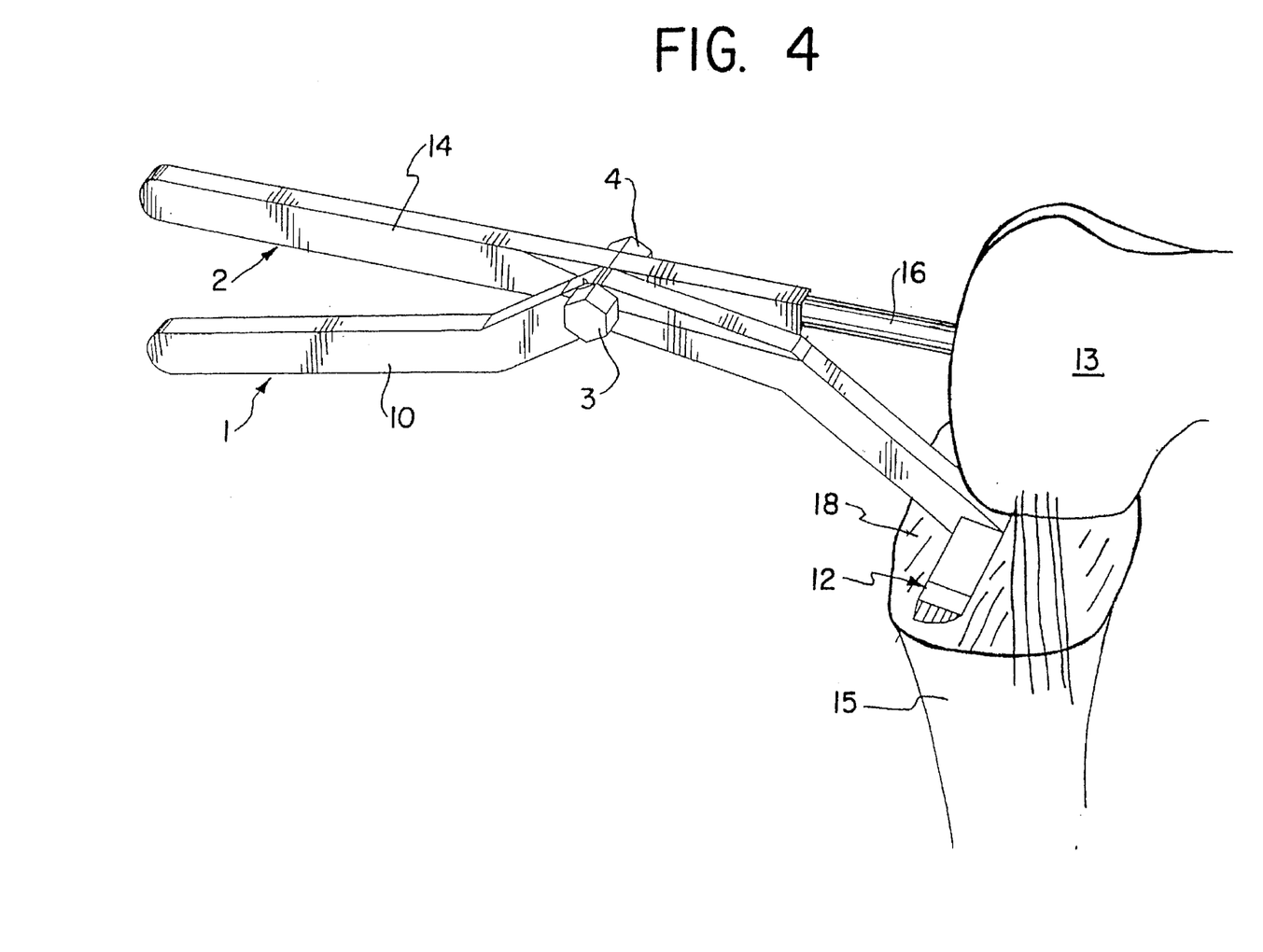
FIG. 4 shows a typical embodiment of the present invention on a flexed knee after application of a distraction force.
Figure 5:
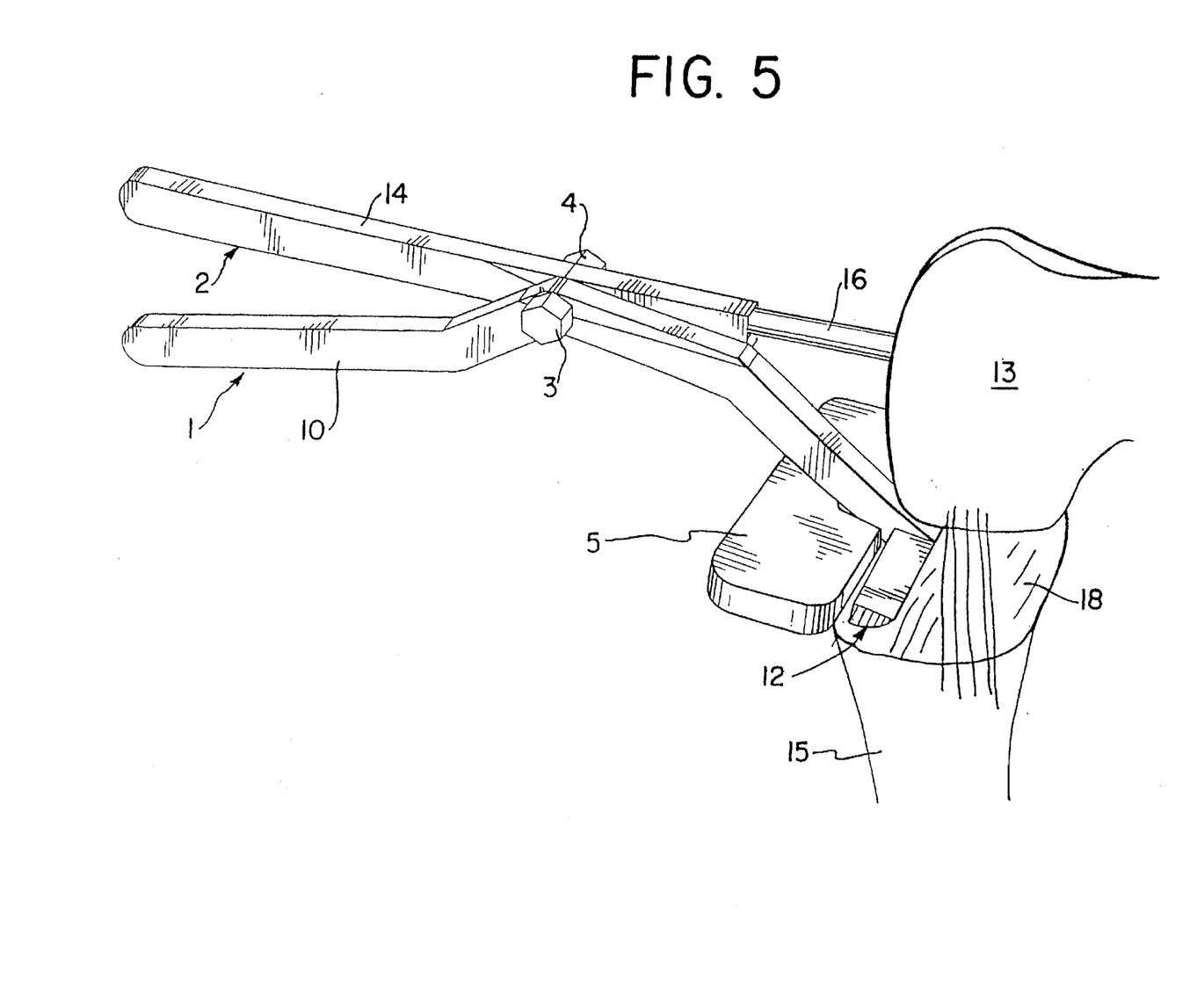
FIG. 5 shows a typical embodiment of the present invention on a flexed knee after application of a distraction force, used in combination with a spacer block to position the posterior femoral cut at a predetermined distance from the cut tibial surface.
Figure 6:
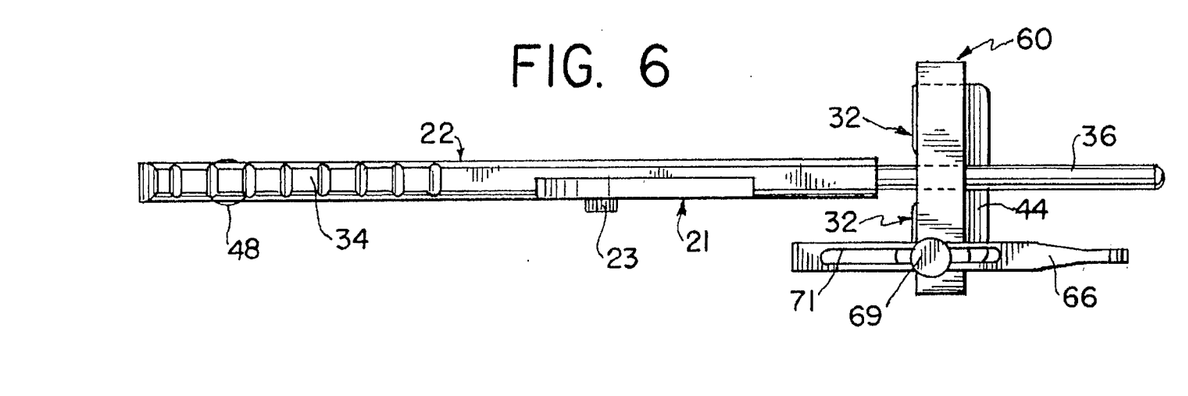
FIG. 6 is a top plan view of a preferred embodiment of the invention having an anterior-posterior chamfer cutting guide mounted thereon.
Figure 7:
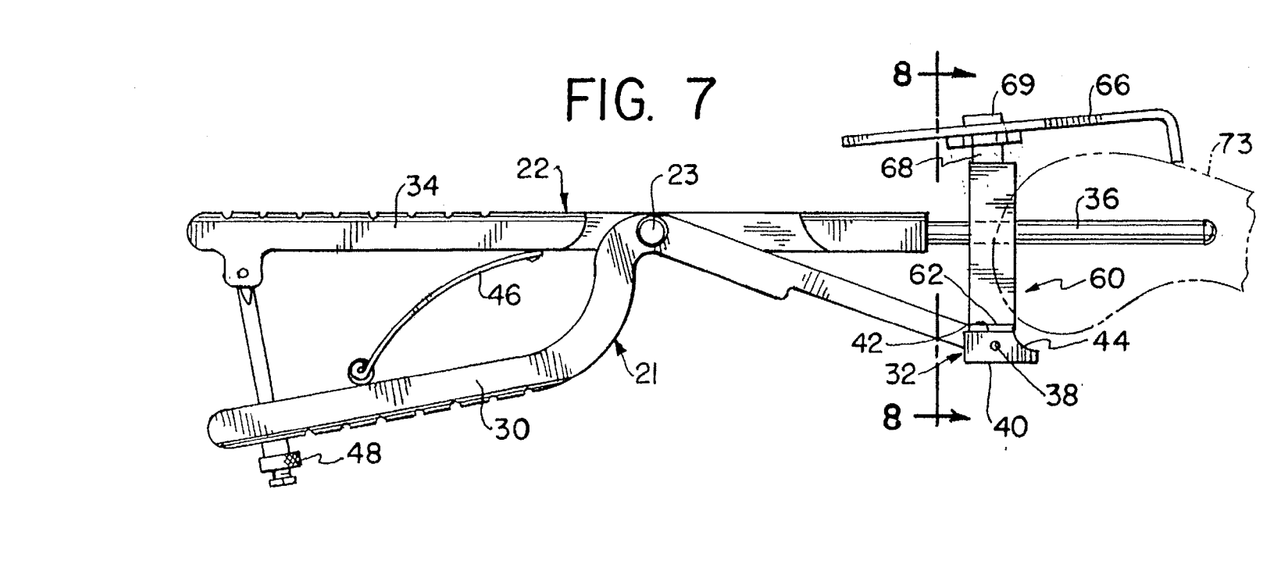
FIG. 7 is a side plan view of the preferred embodiment shown in FIG. 6.
Figure 8:
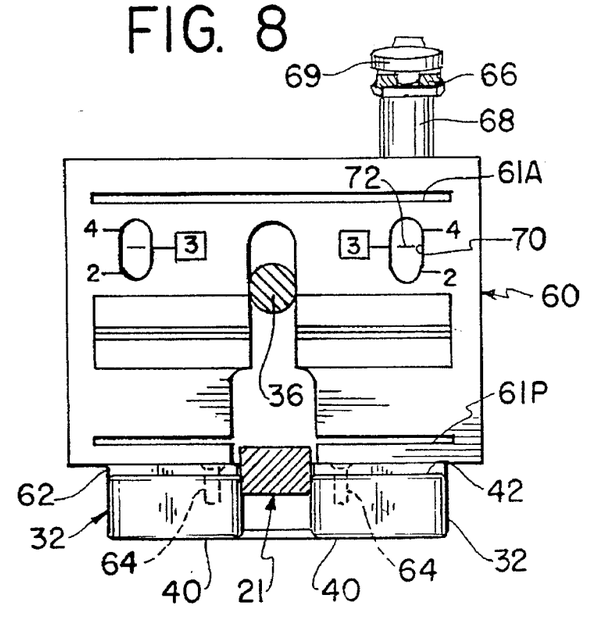
FIG. 8 is a sectional view along the line 8—8 of FIG. 7.
Figure 9:
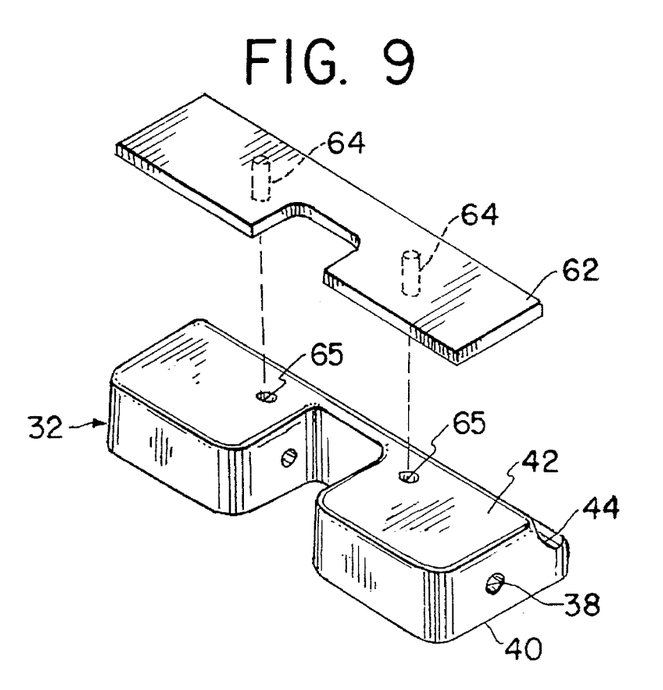
FIG. 9 is an exploded perspective view of the spacer shim and platform used in the preferred embodiment.

FIGS. 3, 4 and 5 show one use of the knee flexion-gap distraction device. The T-shaped platform 12 of tibial device 1 is placed in the center of the cut tibial surface 18, with the knee flexed to 90°. The cylindrical end 16 of femoral device 2 is inserted into a pre-drilled opening (not shown) which leads from the center of the femoral intercondylar notch into the femoral intramedullary canal. The contoured handles 10 and 14 of tibial device 1 and femoral device 2 together form a hand-grip which, when squeezed, applied a distraction force between the distal femur and proximal tibial surface.

The T-shaped platform 12 of tibial device 1 maintains the distal femur centered above the tibia in a medial to lateral direction. The cylindrical end 16 of femoral device 2 lifts the distal femur away from the tibial surface 18 while allowing rotation of the femur 13 around an axis connecting the hip joint and the hole in the intercondylar area of the distal femur into which cylindrical end 16 of femoral device 2 is inserted.

Rotation of the femur 13 around this axis allows approximate equalization of tension applied to the medial and lateral ligaments. Tactile feedback through the hand-held squeeze grip or direct palpation of the knee ligaments will help determine the appropriate amount of distraction force. During maintenance of the distraction force, the optimal anterior-posterior positioning of the femoral components may be measured directly from the cut surface of the tibia.

A spacer block 5 may be placed on the cut tibial surface and used to determine the correct position of the posterior femoral cut. Alternatively, the spacer block 5 could be used as a tibial platform for the knee flexion gap distraction device, with the spacer block 5 and distraction device linked together.

FIGS. 6–9 illustrate a preferred embodiment of the invention in which the platform which engages the tibia articulates or pivots with respect to the tibial lever.

In this embodiment, the tibial component is shown as a lever 21 and the femoral component as lever 22. The levers 21 and 22 are pivotally connected by a nut and bolt (or in any other suitable way) which form an axle 23.

The levers 21 and 22 include handle portions 30 and 34 at one end which can be gripped by the surgeon to separate the opposite ends of the levers when the handles are squeezed. At these opposite ends, tibial lever 21 includes a platform 32 and the femoral lever 22 includes an elongated intramedullary rod 36.

The principle difference between the embodiments of FIGS. 6–9 and the embodiment of FIGS. 1–5 resides in the fact that the tibial platform 32 is connected to the distal end of tibial lever 21 by means of a pin 38 which permits the platform 32 to pivot with respect to the lever. Moreover, the shape of platform 32 is different from the shape of platform 12. Platform 32 includes a flat bottom surface 40 which is adapted to rest on the flat (cut) proximal surface of the tibia, a flat upper surface 42 which supports a cutting guide as described below, and a curved distal face 44 which enables the platform to fit beneath the femoral condyles.

A conventional tension spring 46 and handle screw 48 are provided at the handle end of the instrument. The tension spring biases the handles 30 and 34 apart. The handle screw 48 enables the surgeon to lock the distraction device in position after the knee has been distracted.

Other ways may be provided to lock the instrument into the distracted position in order to free the surgeon's hands so that he or she can position the cutting guide. For example, a ratchet type mechanism similar to that used on lamina spreaders may be used.

The embodiment of FIGS. 6–9 provides advantages as compared to the embodiment of FIGS. 1–5 in that the tibial platform 32 which rests on the cut tibial surface has a larger surface area in contact with the surface of the tibia; thus, it is less likely to indent the relatively soft tibial surface. Moreover, the tibial platform 32 is less likely to move relative to the tibial surface which means that the instrument itself is more stable. Also, and as explained further below, in the embodiment of FIGS. 6–9, the tibial platform itself (with spacer shims, if necessary) positions the cutting guide a predetermined distance from the tibial surface. This allows the surgeon to create a flexion gap of a precise size and shape. In the embodiment of FIGS. 1–5, a separate spacer block is placed on the tibia and used to position the cutting guide. The embodiment of FIGS. 6–9 reduces the number of instrument components used at one time, thereby simplifying the technique.

FIGS. 6–9 also show a representative cutting guide used in conjunction with the invention. The cutting guide 60 is bifurcated (see FIG. 8) so that the intermedullary rod 36 can pass between its two sections. The cutting guide may rest on a flat spacer shim 62 which sits on the upper flat surface 42 of the tibial platform 32. As explained below, the function of the spacer shim 62 is to position the cutting guide 60 relative to the femur (shown in dotted lines) so that the posterior femoral cut will be made at the proper location. Spacer shim 62 may include downwardly depending registration pins 64 which engage complementary holes 65 in the upper surface of platform 32 to retain the spacer shim in position.

The cutting guide 60 includes slots 61A and 61P to guide a cutting tool to make the anterior femoral and posterior femoral cuts, respectively. In addition, slots (not numbered) are provided for the anterior chamfer and posterior chamfer cuts. The use of such cutting guides is conventional.

The cutting guide also includes an outrigger stylus 66 which is adjustably attached to a vertical shaft 68 by a bolt 69 which passes through slot 71 in stylus 66. Shaft 68 is slidably received in a suitable bore (not numbered) within the cutting guide 60. The stylus point should ideally fall to the position of slot 61A (which defines the anterior femoral cut). The actual position of the slot 61A relative to the anterior femoral surface 73 can be determined by the surgeon through a viewing slot or window 70 in the "back" of the cutting guide 60 (see FIG. 8). With the stylus point contacting the anterior femoral surface, the position of slot 61A relative to the anterior femoral surface can be indicated by the position of a mark 72 on shaft 68, which is visible within the window 70, and which represents the point of the stylus, i.e. a point flush with the anterior femoral surface 73. If mark 72 is positioned in the center of window 70, the guide is the proper size for the patient's femur, i.e. the anterior femoral cut will be flush with the femur. If aligned at the top of the window (adjacent numeral "4") or the bottom (adjacent numeral "2"), a different cutting guide is required, the size of which is indicated by the adjacent numeral (i.e. "2" or "4").

The instrument shown in FIGS. 6–9 is used as follows. The tibial cut and the distal femoral cut will have been made in conventional fashion. Osteophytes from the femur and tibia are removed. If a posterior cruciate ligament (PCL) sacrificing implant is to be used, the ligament is then transected. The knee is brought to extension and the extension gap balanced by soft tissue releases. The size and balance of the extension gap is checked with spacer blocks. The spacer block is then removed and the knee flexed to 90°.

It is at this point that the invention is used. The intramedullary rod 36 of femoral lever 22 is placed a short distance into the intermedullary canal of the patient's femur. The tibial platform 32 of the tibial component is then rested on the cut surface of the tibia, with its curved face 44 placed slightly beneath the posterior femoral condyles. The surgeon then squeezes the hand grip 30/34 to separate or distract the flexion gap. The handle nut 48 is then tightened to maintain the distracted position. As explained above, the femur can rotate around the rod 36 so that the medial and lateral sections are equally distracted.

After the ligaments are balanced, a cutting guide 60 is placed over the distractor so that it rests against the cut distal surface of the femur and on the upper surface 42 of the tibial platform. Because of the thickness of the tibial platform, when the cutting guide rests on it, the posterior femoral cut will result in a flexion gap the same size as an 8 mm tibial component. The flexion gap can be adjusted in size for any other tibial component thickness by placing an appropriate spacer shim 62 between the guide 60 and platform 32.

It is also necessary to select a cutting guide 60 of the proper size. The outrigger stylus 66 is used for this purpose. If the indicator mark 72 within window 70 is centered, the cutting guide in position is properly sized, which means that the anterior femoral cut will be made at the proper position relative to the posterior cut for the patient's femur. If the mark is adjacent the numerals "2" or "4" the surgeon knows the size of the cutting guide required to properly place the anterior cut. The fact that the surgeon is provided with an indication of the size of the proper cutting guide is a useful feature of the invention.

If the position of the indicator mark 72 is between sizes, the tension in the flexion gap distractor can be adjusted within reasonable limits to ensure that the anterior cut will be flush with the anterior femur. Adjustment of the flexion gap distractor will affect ligament tension in the flexion gap which is a trade-off that the surgeon must handle.

After the cutting guide has been selected and positioned so that the proper cuts will be provided, the cutting guide is nailed onto the femur (the nail holes are not shown in the drawings). The distractor is then removed and the cuts are made. If a PCL sacrificing implant is to be used, the notch is created with a notch guide.

In the preferred embodiment, the tibial platform is not readily detachable from the tibial lever and spacer shims are used if necessary to properly position the cutting guide. Instead of using a permanent connection, a detachable connection between the tibial lever and tibial platform may be used so that the surgeon would be able to select a tibial platform with the proper dimensions. Different ways can be used to releasably connect the tibial lever and platform. For example, the forward end of the tibial lever may include a transverse cylinder which can be received within a shallow complementary slot in the upper surface of the tibial platform. Alternatively, the forward end of the lever may be pivotally attached to a vertical post which is adapted to fit into a complementary hole in the upper surface of the platform. A simpler construction would be to shape the forward end of the tibial lever so that it fits into a complementary slot within the upper surface of the tibial platform.

The invention thus provides an improved flexion gap distraction device which automatically matches the flexion and extension gaps. It externally rotates the femoral component of the knee because in most cases the medial collateral ligament will be tight and internally rotate the femur relative to the cutting guide. It provides a way to cut the anterior femur flush with the shaft and will work for both PCL retaining and PCL sacrificing knees. With minor modifications the invention should have utility for any brand of knee prosthesis.

The present invention has significant advantages over the prior art. When compared to other joint distractors, the use of femoral rotation to equalize tension among the ligaments eliminates the need for separate distractors for each condyle, thereby greatly simplifying instrument construction and use. When compared to the posterior condyle referencing technique, ligament balancing is more reliable and reproducible, especially in cases of condylar erosion and pre-existing deformity.

While the above description contains many specifities, these should not be construed as limitations on the scope of the invention, but rather as an exemplification of one preferred embodiment thereof. Many other variations are possible. For example, the method of engaging the distal femur may be modified to form a hook which engages the femoral intercondylar notch or modified to form a linkage between an intramedullary rod and the distraction device. The method of engaging the proximal tibia may take the form of a platform or intramedullary rod. The methods of applying, measuring, or maintaining the distraction force may include springs, ratchets, suspended weights, strings, elastic bands, screws, or gear mechanisms. The methods of positioning the posterior femoral cut relative to tibial reference points may include a separate measuring device, extensions of the tibial portion of the distraction device, or guides which are positioned relative to the tibia or the tibial portion of the distraction device. Accordingly, the scope of the invention should be determined not by the embodiments illustrated, but by the appended claims and their legal equivalents.

I claim:

1. A flexion-gap distraction device for use in positioning the femoral and tibial components of a total knee in a total knee arthroplasty, comprising first and second levers pivotally connected at a point intermediate their ends, said first lever including means at its forward end for engaging the distal end of the femur of a flexed knee such that the femur may rotate about an axis between the center of the hip joint and the femoral intercondylar notch area, a tibial platform for engaging the cut surface of the tibia, and said second lever being pivotally connected to said tibial platform at its forward end, whereby pressure applied to the rearward ends of said levers distracts the distal end of the femur and the tibial platform so that the patients medial and lateral knee ligaments may be equally tensioned in flexion.

2. A flexion-gap distraction device according to claim 1, wherein said tibial platform includes flat upper and lower surfaces.

3. A flexion-gap distraction device according to claim 2, wherein said tibial platform includes a curved forward portion adapted to fit between a patient's tibia and the condyles of the femur.

4. In combination, a flexion-gap distraction device according to claim 1 and a cutting guide, said cutting guide resting on the upper surface of said platform.

5. The combination according to claim 4, further including at least one spacer shim between said platform and said cutting guide.

6. The combination according to claim 4, wherein said cutting guide includes a slot through which an anterior femoral cut is to be made in the femur, a stylus having a point adapted to contact the anterior surface of the patient's femur, said stylus being movable with respect to said cutting guide, and means for indicating the position of the stylus point relative to said cutting guide slot.

* * * * *